United States Patent [19]

Cukor et al.

[11] 3,962,298
[45] June 8, 1976

[54] PREPARATION OF HIGHLY SOLUBLE BISMUTH SALTS OF ORGANIC ALKANOIC ACIDS

[75] Inventors: Peter Cukor, Natick; Kurt B. Kilichowski, Lexington, both of Mass.

[73] Assignee: GTE Laboratories Incorporated, Waltham, Mass.

[22] Filed: July 24, 1974

[21] Appl. No.: 491,186

[52] U.S. Cl. ............................... 260/447; 252/300
[51] Int. Cl.$^2$ .......................................... C07F 7/94
[58] Field of Search ............. 260/447, 414; 252/300

[56] References Cited
UNITED STATES PATENTS

| | | | |
|---|---|---|---|
| 2,198,357 | 4/1940 | Vargha | 260/447 |
| 3,211,768 | 10/1965 | Considine | 260/447 X |
| 3,350,436 | 10/1967 | Leebrick | 260/447 X |

OTHER PUBLICATIONS

Chemical Abstracts, vol. 35, 5070$^4$ (1941).
Chemical Abstracts, vol. 34, 5049$^2$ (1940).

*Primary Examiner*—Helen M. S. Sneed
*Attorney, Agent, or Firm*—Irving M. Kriegsman

[57] ABSTRACT

Highly soluble bismuth salts of organic alkanoic acids are prepared by reacting an organic triaryl bismuth compound with an alkanoic acid in an inert organic solvent, and, after essential completion of the reaction, removing the inert organic solvent to afford the desired bismuth salt.

2 Claims, No Drawings

PREPARATION OF HIGHLY SOLUBLE BISMUTH SALTS OF ORGANIC ALKANOIC ACIDS

FIELD OF THE INVENTION

This invention relates to the preparation of metal salts of organic acids. More particularly, this invention relates to the preparation of bismuth salts of organic alkanoic acids. The salts so prepared are highly soluble in certain solvent materials and, thus, are suitable for use in the preparation of lusters to be applied to the faceplates of cathode ray tubes intended, for example, for television use.

BACKGROUND OF THE INVENTION

In the process of decorating glass or ceramic substrates with colored films, resinates and/or lusters may be used. Resinates are metal salts (soaps) of organic acids dissolved in an appropriate solvent mixture, such as an essential oil (e.g., pine oil, rose oil, clove oil, jasmine oil, etc.) mixed with xylene, toluene and/or other hydrocarbons. Lusters are mixtures of resinates blended to produce a given colored film. Resinates and/or lusters are prepared on the substrate and the coated substrate fired in an oven. The organic material decomposes to products which readily evaporate at the firing temperatures, while the inorganic material, in the resinates and/or lusters, adheres to the substrate surface as a thin colored film. Certain metal resinates present in lusters do not directly contribute to color formation, but their presence is necessary for flux formation, for colloidal dispersion, and for improved properties of the final films. Bismuth salts (resinates) are of interest because they can be blended with other salts to give either blue or green lusters.

Presently, there are numerous efforts being made to develop a "black beauty" type colored television cathode ray tube. A black beauty type faceplate consists of a dot pattern of filters arranged in such a manner that in front of each phosphor dot, there is a filter which transmits the light emitted from the phosphor and absorbs all other wavelengths of light. Thus, in front of a blue emitting phosphor dot, there will be a blue colored filter. One of the most convenient ways of preparing a faceplate with tri-dot filters is by using lusters. In certain attempts to prepare black beauty type faceplates, commercially available lusters were used. It was found, however, that the spectral characteristics of the filters thus prepared were not optimal for the intended use. To compensate for this deficiency, it was believed necessary to prepare the individual metal salts, test them to obtain their spectra, and then mix them in various proportions to thereby provide lusters having better spectral characteristics. Early attempts to prepare satisfactory bismuth salts were unsuccessful, since even if the salt was formed, it was an insoluble precipitate, soluble at the most to about 5.8 percent, which is considerably less than the 20 percent solubility present in the commercially available resinate and which is needed for the use contemplated, by the present invention, in luster mixtures.

OBJECTS OF THE INVENTION

It is, therefore, an object of this invention to provide a process for preparing highly soluble bismuth salts of organic alkanoic acids.

A further object of this invention is to provide novel bismuth salts of organic acids.

A still further object of this invention is to provide a highly soluble preparation including the novel bismuth salts of the present invention.

These and still further objects, features, and advantages of the present invention will become apparent upon consideration of the following detailed disclosure.

SUMMARY OF THE INVENTION

These and still further objects, features, and advantages of the present invention are achieved, in accordance therewith, by reacting an organic triaryl bismuth compound with an alkanoic acid in an inert organic solvent, and, after at least essential completion of the reaction, removing the solvent to afford the desired product consisting essentially of the bismuth (+3) salt of the alkanoic acid. In one embodiment of the invention, the triaryl bismuth compound is reacted with an excess of the alkanoic acid in which case the product will consist of a major amount of the bismuth (+3) salt of the alkanoic acid in admixture with a minor amount of excess (i.e., unreacted) alkanoic acid. As used herein, "excess" refers to up to about 10 percent of unreacted alkanoic acid of the stoichiometrically required amount for complete reaction. This product need not be purified prior to use in luster preparations since the minor amount of the free alkanoic acid has been found to enhance or improve the solubility of the resultant bismuth salt.

In other embodiments, the bismuth compound and the alkanoic acid are used in stoichiometric amounts or the bismuth compound is used in excess. Stoichiometric as used herein, refers to a molar ratio of 1 mole of the triaryl bismuth compound to 3 moles of the alkanoic acid. Since, when the aforementioned reaction is allowed to go to completion, the bismuth atom is substituted for one of 3 hydrogen atoms on each of the three alkanoic acids to thereby afford the resultant product represented by the formula $Bi(RCOO)_3$.

As used in this specification, "aryl" means phenyl or naphthyl optionally substituted with one or more alkyl ($C_{1-6}$), hydroxy, amino, or trifluoromethyl groups; and "alkanoic acid" means a straight or branched chain aliphatic acid having 5 to 20 carbon atoms, such as, for example, pentanoic acid, hexanoic acid, octanoic acid, 3,5,5-trimethylhexanoic acid, decanoic acid, dodecanoic acid, hexadecanoic acid, octadecanoic acid, and eicosanoic acid and the like. The reaction is conducted in an inert organic solvent, such as acetone, benzene, toluene, p-butyl-benzene, and the like, at room temperature to the reflux temperature of the particular solvent or solvent system utilized, preferably at the reflux temperature of the solvent material for about 4 to 24 hours, or until the reaction is at least essentially completed. Thereafter, the solvent is removed to leave the bismuth (+3) salt of the alkanoic acid, in combination, in the preferred embodiment hereof, with a minor amount of the free alkanoic acid, which is not removed as it enhances or improves the solubility of the bismuth salt in the preparation of suitable lusters. The triaryl bismuth reactant is particularly suited for use in the process of this invention because it does not explode on decomposition when heated in the course of the reaction described above. This feature distinguishes the process of this invention from any prior art process where undesirable explositions or decompositions occur, thus preventing the preparation of the desired product.

The resultant bismuth salt of the alkanoic acid is blended with other metallic salts ("soaps" or "resinates") in desired proportions, by conventional techniques, to provide lusters, and films prepared from the resultant lusters are equivalent to films produced using commercial lusters, but have better spectral characteristics.

DESCRIPTION OF SPECIFIC EMBODIMENTS

The following specific description is given to enable those skilled in the art to more clearly understand and practice the present invention. It should not be considered as a limitation of the scope of the invention, but merely as being illustrative and representative thereof.

EXAMPLE I 8.8 Gm (.02M) of triphenyl bismuthine and 20 gm. of acetone are added to a 0.25 liter round bottom flask, and the flask is swirled to dissolve the triphenyl bismuthine in the acetone. 10.49 Gm (0.06 M + 1 gm. excess) of 3,5,5-trimethylhexanoic acid is added to the flask and reaction mixture if heated at reflux, with stirring, for 4-6 hours. The solvent is removed by use of a rotary flash evaporator to yield the bismuth (+3) slat of 3,5,5-trimethylhexanoic acid in admixture with a small amount of 3,5,5-trimethylhexanoic acid.

EXAMPLE II

Example I is repeated with similar results substituting toluene for acetone as the solvent material.

EXAMPLE III

In similar manner to the procedure of Examples I and II, substituting pentanoic acid, hexanoic acid, octanoic acid, decanoic acid, dodecanoic acid, hexadecanoic acid and octadecanoic acid for the 3,5,5-trimethylhexanoic acid, the corresponding bismuth (+3) slats of the respective alkanoic acids are prepared.

EXAMPLE IV

A blue luster is prepared having the following composition:
   Gold organic compound containing 1.5 gr. gold;
   Silver organic compound containing 2.99 gr. silver;
   Bismuth salt of Example I containing 4.00 gr. bismuth;
   Solvent comprising mixture of toluene, xylene, pine oil and turpentine (to 100 gr.).

EXAMPLE V

A green luster is prepared having the following composition:
   Gold organic compound containing 2.09 gr. gold;
   Chromium organic compound containing 1.15 gr. chromium;
   Bismuth compound of Example I containing 13.2 gr. bismuth;
   Solvent mixture comprising toluene, xylene, pine oil and turpentine (to 100 gr.).

In preparing the lusters of Examples IV and V above, it is noted that no precipitate forms when the products of Examples I or II are added to the solvent system. In addition, the bismuth salt of the present invention is stable upon standing whereas other commercially available resinates were unstable.

While the present invention has been described with reference to specific embodiments thereof, it should be understood by those skilled in this art that various changes may be made and equivalents may be substituted without departing from the true spirit and scope of the invention. In addition, modifications can be made to adapt a particular situation, material or composition of matter, process, process step or steps, or then-present objective to the spirit of this invention without departing from its essential teachings.

What is claimed is:

1. A composition of matter consisting essentially of a major amount of bismuth (+3)-3,5,5-trimethylhexanate and a minor amount of 3,5,5-trimethylhexanoic acid.

2. The composition of claim 1 comprising about 18 to 25 percent bismuth (+3)-3,5,5-trimethylhexanate and about 2 to about 10 percent of 3,5,5-trimethylhexanoic acid.

* * * * *

UNITED STATES PATENT OFFICE
CERTIFICATE OF CORRECTION

Patent No. 3,962,298     Dated June 8, 1976

Inventor(s) Peter Cukor and Kurt B. Kilichowski

It is certified that error appears in the above-identified patent and that said Letters Patent are hereby corrected as shown below:

Column 1, line 46, place black beauty within quotation marks.
Column 3, line 20, "if" should read --is--.
Column 3, line 22, "slat" should read --salt--.
Column 3, line 35, "slats" should read --salts--.

Signed and Sealed this

Twelfth Day of October 1976

[SEAL]

Attest:

RUTH C. MASON
Attesting Officer

C. MARSHALL DANN
Commissioner of Patents and Trademarks